United States Patent [19]

Suciu-Foca et al.

[11] Patent Number: 5,066,581
[45] Date of Patent: Nov. 19, 1991

[54] DIFFERENTIATION ANTIGEN, NDA$_3$, ASSOCIATED WITH THE RECEPTOR FOR B CELL GROWTH FACTOR

[75] Inventors: Nicole Suciu-Foca, Cliffside Park, N.J.; Donald W. King, Chicago, Ill.

[73] Assignee: The Trustees of Columbia University in the City of New York, New York, N.Y.

[21] Appl. No.: 11,004

[22] Filed: Feb. 5, 1987

[51] Int. Cl.$^5$ .................. C07K 15/06; C07K 15/28; G01N 33/567; G01N 33/577
[52] U.S. Cl. .................. 435/7.24; 435/172.2; 435/240.27; 435/948; 436/503; 436/548; 436/811; 530/350; 530/387; 530/395; 530/806; 530/809; 530/827; 935/110
[58] Field of Search .............. 435/172.2, 240.27, 948, 435/7.24, 34, 7; 436/501, 506, 519, 548, 811, 543; 530/350, 387, 806, 809, 395, 827; 935/104, 110

[56] References Cited

U.S. PATENT DOCUMENTS 4,692,405 9/1987 Freedman et al. .................. 435/110

OTHER PUBLICATIONS

Suzuki et al., *Journ. Immunol*, 137, 1208–1213, 1986.
Suciu-Foca et al., *Immunol. Res.*, 5, 165–172, 1986.
Suzuki et al., *Fed. Proceed.*, 44, 1328, Abstr. No. 5364, 1985.
Yakura et al., *Fed. Proceed.*, 44, 1532, Abstr. No. 6558, 1985.
Cambier, *Nature*, 319, 620, 1986.
Greenwood et al., *Immunology*, 59, 7–23, 1986.
Jung et al., *Journ. Exp. Med.*, 160, 1919–1924, 1984.
Kikutani et al., *Journ. Immunol.*, 136, 4019–4026, 1986.
LePrince et al., *Journ. Immunol.*, 140, 100–107, 1988.
Pearson et al., *Meth. Enzymol.*, 92, 196–220, 1983.
Roitt, *Essential Immunology*, 5th Ed., Blackwell Scientific Publication, Oxford, 1984, pp. 68, 70, 326 and 327.

*Primary Examiner*—David A. Saunders
*Attorney, Agent, or Firm*—John P. White

[57] ABSTRACT

This invention provides a purified new differentiation antigen, designated NDA$_3$, associated with the growth and proliferation of activated B lymphocytes and characterized by a molecular weight of about 36,000 daltons.

The invention also provides an antibody capable of specifically forming a complex with purified NDA$_3$. Another aspect of the invention provides a hybridoma which produces a monoclonal antibody that specifically recognizes the isolated NDA$_3$.

The invention also pertains to a method for detecting B cells or helper T cells, each of which has a B cell growth factor receptor, which comprises contacting a sample which contains B cells or helper T cells with substances capable of forming complexes with the B cell growth factor receptors so as to form cellular complexes between the substances and the B cell growth factor receptors, and detecting such cellular complexes.

11 Claims, 5 Drawing Sheets

DIFFERENTIATION ANTIGEN, NDA$_3$, ASSOCIATED WITH THE RECEPTOR FOR B CELL GROWTH FACTOR

BACKGROUND OF THE INVENTION

Within this application several publications are referenced by Arabic numerals. Full citations for these references may be found at the end of the specification immediately preceding the claims. The disclosures of these publications in their entirety are hereby incorporated by reference into this application in order to more fully describe the state of the art to which this invention pertains.

The transition of T and B lymphocytes from their resting state to a state of functional maturity involves distinct steps of activation, proliferation and differentiation, each requiring specific signals.

Activation is initiated after antigens, mitogens or antibodies interact with the T-cell antigen receptor complex or with B-cell-surface immunoglobulins.

Activated T lymphocytes produce the growth promoting lymphokine interleukin-2 (IL-2) and express high affinity receptors for IL-2. For clonal expansion, and thus for specific T-cell immune responses to take place, the IL-2 receptor must interact with IL-2.

Similarly, the proliferation and subsequent differentiation of B lymphocytes is also regulated by at least two distinct types of lymphokines: one which promotes their growth (B cell growth factor or BCGF) and the other their differentiation into immunoglobulin secreting cells (B cell differentiation factor or BCDF) [1-4]. These lymphokines are produced primarily by T lymphocytes although B cells activated with Staphylococcus aureus Cowan 1 (SAC) [5,6] or transformed with Epstein Barr Virus (EBV) are also capable of secreting autocrine growth factors [6,10]. Recently some of those factors have been characterized biochemically, and the gene coding the synthesis of at least one of them has been cloned [4]. However, the molecular structure of the B cell receptor(s) for growth and differentiation factors is still unknown.

The identification and characterization of such receptors is of obvious importance for understanding the mechanisms which regulate the growth and differentiation of B-lymphocytes.

Several studies have reported on monoclonal antibodies specific for resting [22,23] or for activated B lymphocytes [24] that inhibit [23,24] or, alternatively, promote [22] the activation and differentiation of B lympoocytes. Monoclonal antibodies reacting with molecules involved in leukocyte cell interaction were also shown to mimic the biological effects of B cell stimulatory factors suggesting that they react with molecules associated with BCGF-receptor structures [25].

However, none of these monoclonal antibodies blocked the receptor of activated B cells for BCGF or BCDF. Monoclonal antibody (MoAb) NDA$_3$ fulfills this essential criterion on which the definition of a receptor depends, i.e. it inhibits the interaction of the receptor with its ligand.

The newly developed MoAb NDA$_3$ provides a tool for studying the mechanism of BCGF-R expression and internalization and of transmission of the proliferation signal.

SUMMARY OF THE INVENTION

This invention provides a purified new differentiation antigen, designated NDA$_3$, associated with the growth and proliferation of activated B lymphocytes and characterized by a molecular weight of about 36,000 daltons. In one embodiment of the invention the antigen is expressed by activated human B lymphocytes and comprises at least a portion of the B cell receptor polypeptide for B cell growth factor.

The invention also provides an antibody capable of specifically forming a complex with purified NDA$_3$. Another aspect of the invention provides a hybridoma which produces a monoclonal antibody that specifically recognizes the isolated NDA$_3$.

The invention also pertains to a method for detecting B cells or helper T cells, each of which has a B cell growth factor receptor, which comprises contacting a sample which contains B cells or helper T cells with substances capable of forming complexes with the B cell growth factor receptors so as to form cellular complexes between the substances and the B cell growth factor receptors, and detecting such cellular complexes. Another embodiment of the invention also provides a method of evaluating B cell or helper T cell activity which comprises isolating peripheral blood mononuclear cells, treating the cells with a monoclonal antibody capable of specifically forming a complex with the isolated NDA$_3$, and determining the amount of monoclonal antibody bound to the cells.

The invention also involves a method for diagnosing an immune system abnormality in a subject which comprises determining the number of B cells or helper T cells in a sample from the subject, contacting the sample with substances capable of forming complexes with the B cell growth factor receptors so as to form complexes between the substances and B cell growth factor receptors, determining the percentage of B cells or helper T cells in the sample which have the B cell growth factor receptor and comparing the percentage so determined with the percentage of cells which have the B cell growth factor receptor in a sample from a normal subject who does not have the immune system abnormality, a difference in the percentage of cells so determined being indicative of the immune system abnormality.

BRIEF DESCRIPTION OF THE FIGURES

FIG. 3—Binding of $^{125}$I-labelled MoAb NDA$_3$ to LBCL and blocking by human BCGF-12 kd.

FIG. 4—Panel A: Analysis of NDA$_3$ antigen by SDS-PAGE.

Panel B: Western Blot Analysis of NDA$_3$ antigen.

Panel C: Western Blot Analysis with $^{125}$I-labelled MoAb NDA$_3$.

DETAILED DESCRIPTION OF THE INVENTION

This invention provides a purified new differentiation antigen, designated NDA$_3$, associated with the growth and proliferation of activated B lymphocytes and characterized by a molecular weight of about 36,000 daltons. Preferably, the activated B lymphocytes are human B lymphocytes.

A hybridoma cell line which produces MoAb NDA$_3$ was deposited Feb. 25, 1987 pursuant to, and in satisfaction of the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. HB 9334.

The possibility that NDA$_3$ serves as, or comprises at least a portion of, a B cell growth factor (BCGF) receptor is suggested by three lines of evidence: (1) MoAb NDA$_3$ inhibits the activation by *Staphylococcus aureus Cowan I* (SAC) of resting peripheral blood B lymphocytes possibly by blocking the access to the BCGF receptor of endogenous BCFG; (2) similarly, Epstein Barr virus (EBV)-transformed B lymphoblasts pretreated with MoAb NDA$_3$ show a decreased capacity to respond to exogenous BCGF suggesting that the antibody blocks the BCGF receptor; and (3) both SAC-activated and EBV-transformed B cells exhibit an enhanced capacity to grow if cultured in medium containing MoAb NDA$_3$. Under these latter conditions, binding of the antibody to its receptor may result in BCGF receptor internalization and transmission of the proliferation signal, much in the way in which BCGF itself is expected to operate. Preferably, the BCGF receptor is a human BCGF receptor specific for human BCGF-12 kd.

The invention also provides an antibody capable of specifically forming a complex with purified NDA$_3$. Preferably, the antibody is a monoclonal antibody.

NDA$_3$ polyclonal antibodies can be produced by immunizing animals with isolated NDA$_3$ by conventional techniques to produce polyclonal NDA$_3$ monoclonal antibody antisera.

NDA$_3$ monoclonal antibodies can be produced by antibody-producing cell lines. NDA$_3$ monoclonal antibody producing cell lines may be hybridoma cell lines commonly known as hybridomas. The hybrid cells are formed from the fusion of an NDA$_3$ monoclonal antibody-producing cell and an immortalizing cell line, that is, a cell line which imparts long term tissue culture stability on the hybrid cell. In the formation of the hybrid cell lines, the first fusion partner, the NDA$_3$ monoclonal antibody-producing cell, may be a spleen cell of an animal immunized against NDA$_3$. In one embodiment of the invention, the NDA$_3$ monoclonal antibody is produced by a hybridoma cell line designated CU-965.

Alternatively, the NDA$_3$ monoclonal antibody-producing cell may be an NDA$_3$ monoclonal antibody-generating B lymphocyte obtained from the spleen, peripheral blood, lymph nodes or other tissue. The second fusion partner, the immortal cell, may be a lymphoblastoid cell or a plasmacytoma cell such as a myeloma cell, itself an antibody-producing cell but also malignant.

Murine hybridomas which produce NDA$_3$ monoclonal antibodies are formed by the fusion of mouse myeloma cells and spleen cells from mice immunized against NDA$_3$.

The hybridomas are then screened for production of antibody reactive with NDA$_3$. Those hybridomas which produce antibodies reactive with NDA$_3$ are identified and cloned.

Another way of forming the NDA$_3$ monoclonal antibody cell line is by transformation of antibody-producing cells. For example, an NDA$_3$ monoclonal antibody-producing B lymphocyte obtained from a human subject immunized against NDA$_3$, may be infected and transformed with a virus such as the Epstein-Barr virus in the case of human B lymphocytes, to give an immortal NDA$_3$ monoclonal antibody-producing cell. Additionally, B lymphocytes may be transformed by a transforming gene or transforming gene product rather than by infection with Epstein-Barr virus.

The invention also pertains to a method for detecting B cells or helper T cells, each of which has a BCGF receptor, which comprises contacting a sample which contains B cells or helper T cells with substances capable of forming complexes with the BCGF receptors so as to form cellular complexes between the substances and the BCGF receptors, and detecting such cellular complexes. Another embodiment of the invention provides a method of evaluating B cell or helper T cell activity which comprises detecting B cells or helper T cells, each of which has a BCGF receptor, according to the method described above.

In the preferred embodiments, the substances are capable of forming complexes only with the BCGF receptors present on the surface of B cells or helper T cells in which the receptors were expressed. Particularly preferred are substances which comprise NDA$_3$.

One embodiment of the invention provides a method of evaluating B cell or helper T cell activity which comprises:

a. isolating peripheral blood mononuclear cells;

b. treating the cells with the monoclonal antibody of NDA$_3$; and c. determining the amount of monoclonal antibody bound to the cells.

The invention also involves a method for diagnosing an immune system abnormality in a subject which comprises determining the number of B cells or helper T cells in a sample derived from the subject, contacting the sample with substances capable of forming complexes with the BCGF receptors so as to form complexes between the substances and BCGF receptors, determining the percentage of B cells or helper T cell in the sample which have the BCGF receptor and comparing the percentage so determined with the percentage of cells which have the BCGF receptor in a sample from a normal subject who does not have the immune system abnormality, a difference in the percentage of cells so determined being indicative of the immune system abnormality. Preferably, the subject is an animal, e.g., a human.

The invention also pertains to a nucleic acid molecule encoding NDA$_3$, particularly a DNA molecule, and to nucleic acid molecules which are complementary to the nucleic acid molecule encoding NDA$_3$.

As a molecule associated with B cell and helper T cell function, the measurement of NDA$_3$ expression has diagnostic importance. Because NDA$_3$ is distinctive to activated B cells or helper T cells, it is a unique marker for these cells in a population of lymphocytes.

Moreover, the level of expression of NDA$_3$ provides a measure of B cell or helper T cell activity. This information may be important for evalutating the immune status of an individual. For instance, in the treating of certain diseases, such as cancer, agents which affect the immunocompetency are often used. Assays for NDA$_3$ expession may allow physicians to monitor the immune status of the patient and to adjust treatment to minimize the risk of opportunistic infection, often a threat to immunocompromised patients.

Assays for NDA$_3$ expression may be conventional immunochemical assays for cell surface antigens. Peripheral blood mononuclear cells can be isolated from a patient and incubated with NDA$_3$ monoclonal antibody under conditions which allow the antibody to bind the surface antigen. Antibody bound to the cell surface provides a measure of NDA$_3$ expression. Binding of the antibody to cells may be evaluated by employing an NDA$_3$ monoclonal antibody labeled with a radioactive, fluorescent or other compound capable of being detected.

Certain embodiments of this invention are exemplified in the Examples and Experimental Discussion which follow. In these sections, possible mechanisms and structures are postulated. The Examples and the Experimental Discussion are set forth to aid in an understanding of the invention but are not intended to, and should not be construed to, limit in any way the invention as set forth in the claims which follow.

EXAMPLE 1

Production of NDA$_3$ Monoclonal Antibody

BALB/C mice were immunized with four injections of $10^7$ cells from an alloreactive helper T cell clone. Fusions were performed as previously described [11]. Supernatants were tested for reactivity by cytofluorometry using as targets resting and activated monocytes, T and B lymphocytes as well as a variety of normal and malignant lymphoid cell lines. The NDA$_3$ hybridoma was selected for subcloning and characterization because its supernatant reacted with a small proportion (less than 30%) of in vitro activated peripheral blood lymphocytes (PBL) with certain T cell clones producing helper factors and with monoclonal and polyclonal lymphoblastoid cell lines infected with Epstein Barr Virus (EBV). The antibody did not bind to T cells, B cells or monocytes obtained from fresh peripheral blood, lymph nodes, spleen or tonsils. The MoAb NDA$_3$ is of IgM isotype as determined by Ouchterlony test and was purified from supernatants on a Sephacryl-S-300 column (Pharmacia, Uppsala, Sweden), which was washed with chloroform in endotoxin-free water. Purified immunoglobulin (Ig) quantitated by ELISA was used in most experiments.

EXAMPLE 2

Immunofluorescence studies of cell surface distribution of NDA$_3$ antigen

The cell surface distribution of NDA$_3$ antigen was determined by direct immunofluorescence on an Ortho Spectrum III cytofluorograph. Direct staining of cells was performed by incubating $2 \times 10^5$ cells with antibodies conjugated to fluorescein-5-isothiocyanate [12], followed by three washings. Similar studies were performed by radioimmunoassay with $^{125}$I-labelled antibodies [13].

EXAMPLE 3

Determination of the effect of MoAb NDA$_3$ on B cell reactivity to SAC

Peripheral blood lymphocytes were isolated by Ficoll-Hypaque gradient centrifugation and depleted of monocytes by adherence to plastic for 16 hours. "Resting" B cells (Br) were purified on a nylon-wool column. Br were suspended in RPMI 1640 medium supplemented with 10% fetal calf serum (Hyclone-FCS-Logan, Utah) antibiotics and glutamine at a concentration of $2 \times 10^6$ cells/ml. Br were plated in 96-flat bottom wells in a volume of 0.1 ml to which an equal volume of 0.1% SAC or medium only was added.

Activated B cells (Ba) were obtained from cultures stimulated with SAC for 3-days, as described above.

MoAb NDA$_3$ or MoAb LC, which was used as an isotype control, were added to triplicate reactions at a final concentration of 2.5 $\mu$g/ml. Cultures were labelled with $^{3H}$-TdR after 48 hours and harvested 16 hours latter. Purified IgM from MoAbs added to cultures were free of mycoplasma as determined by hybridization with $^3$H-DNA probe homologous to mycoplasma and Acholeplasma ribosomal RNA (Mycoplasma TC Detection Kit, Gen-Probe, San Diego, Calif.). There were no endotoxins in the Ig solution as measured by use of the Limulus Amebocyte Lysate Pyrotell test (Associates of Cape Cod, Inc., Woods Hole, Mass.).

EXAMPLE 4

Determination of the level of $\mu$ chain message in 3D8 cells by slot blot analysis Fifteen million cells from an IgM producing monoclonal B cell-line (LBCL-3D8 cells) were homogenized in 4 M guanidine thiocyanate and RNA was purified by centrifugation through CsCl followed by denaturation in formaldehyde [14].

RNA (10, 5, 2.5, 1, 0.5, 0.25, 0.10 and 0.05 $\mu$mg) was then transferred to a nitrocellulose filter using a slot blot apparatus. Hybridization was to a $^{32}$P-labelled EcoRl fragment of clone CH4-51 which contains the immunoglobulin $\mu$-chain gene.

EXAMPLE 5

SDS-polyacrylamide gel electrophoresis (PAGE) of $^{125}$I-labelled membrane proteins Twenty million cells from a lymphoblastoid cell line (LBCL-RC) were surface labelled with $^{125}$Iodine (Amersham) using the lactoperoxidase method. The labelled cells were washed and lysed in 1% Nonidet P-40 (Sigma), 10 mM Tris with 150 mM NaCl, 0.1% bovine serum albumin (Sigma) and 1 mM phenylmethanesulphonyl fluoride (PMSF) (Sigma) buffer (pH 8.21). The lysate was centrifuged at 20,000 g and the supernatant was precleared three times with rabbit-anti-mouse IgM (Jackson Lab, Avondale, Pa.) coupled to CNBr-activated Sepharose 4B (Pharmacia, Uppsala, Sweden). The precleared cell lysate was then incubated for 2 hours at 4° C. with MoAb NDA$_3$ coupled to Sepharose 4B. After centrifugation, the pellet was washed three times in 0.5 M NaCl and three times in 0.15 M NaCl lysis buffer (pH 8.2), dissolved in SDS-PAGE sample buffer (TRIS-HCL, pH 6.8) and boiled for 5 minutes. The electrophoresis was performed on 12.5% SDS-polyacrylamide gels [15]. Following electrophoresis, the gel was intensified and autoradiographed with Kodak XAR-5 film.

EXPERIMENTAL DISCUSSION

Protein-kinase-C activation is involved in the expression of the NDA$_3$ antigen on activated B lymphocytes The NDA$_3$ antigen was found on SAC-activated B cells, EBV-transformed lymphoblastoid B cell lines (LBCL), T cell clones with helper activity, HTLV-1-infected T cell lines (TCL), and Molt IV TCL. This antigen is not present on the membrane of activated monocytes or of cells of non-lymphoid origin (fibroblasts, colon, lung and breast carcinoma cell lines) or on the surface of resting lymphocytes. Similar to other differentiation antigens, the $NDA_3$ antigen is not expressed on PBL when cells are treated shortly after activation with mitomycine C or emetine-HCl [16,17], indicating that cell proliferation and protein synthesis are required for its expression.

To determine whether protein kinase-C (PKC) activation is involved in the expression of this antigen, cells ($1 \times 10^6$/ml) from two different lymphoblastoid B cell lines were incubated with 12-o-tetradecanoyl-phorbol-13-acetate (TPA) (50 ng/ml) and monitored by direct immunofluorescence for $NDA_3$ expression [18,19]. The density of $NDA_3$ was down regulated within 1 hour from 4686 sites to 3074 sites, as calculated from the product between the number of positive cells and the mean channel of fluorescence. Thus, similar to other receptors, $NDA_3$ is modulated by TPA presumably through phosphorylation via PKC [19].

MoAb $NDA_3$ inhibits the proliferation of resting B cells in response to SAC yet stimulates the growth of SAC activated lymphocytes Since the $NDA_3$ antigen is expressed on SAC-activated B lymphoblasts, the effect of MoAb $NDA_3$ on B cell activation by SAC was studied.

TABLE 1

Effect of MoAb $NDA_3$ on Resting and Activated B Lymphocytes

| Cultures | MoAb Added $NDA_3$ | LC | $^3$H-TdR Incorporation (cpm) Experiment No. 1 | 2 | 3 |
|---|---|---|---|---|---|
| Br | — | — | 1586 | 2706 | 1331 |
| Br | + | — | 2304 | 2902 | 2494 |
| Br | — | + | 1966 | 3032 | 2510 |
| Br + SAC | — | — | 30082 | 48284 | 39530 |
| Br + SAC | + | — | 7472 | 18596 | 22964 |
| Br + SAC | — | + | 30274 | 47648 | 41972 |
| Ba | — | — | 8889 | 9764 | 4534 |
| Ba | + | — | 20681 | 18966 | 19180 |
| Ba | — | + | 9900 | 10946 | 4106 |

The peak of blastogenic response to SAC occurs after 64 hours and then wanes over the following 3 to 4 days. When added to cultures containing resting peripheral blood B lymohocytes (Br), MoAb $NDA_3$ inhibited the blastogenic response of these cells to SAC as determined by quantitating the amount of tritiated thymidine ($^3$H-TdR) incorporated after 64-hours. However, when MoAb $NDA_3$ was added to activated B cells (Ba), that have been already stimulated with SAC for 64 hours, the antibody promoted their growth over the additional 3 days of observation. MoAb-LC, used as an isotype control, had no effect on the blastogenic response of Ba or Br.

Quantitation of the amount of MoAb $NDA_3$ which triggers the proliferation of SAC-activated B cells showed a dose-dependent augmentation of $^3$H-TdR incorporation within the range of 0.5 to 2.5 μg/ml. Lower concentrations of MoAb were not stimulatory, and a plateau was reached at higher concentrations.

SAC-activated B cells produce BCGF within the first 12 to 24 hours, and then seem to autoutilize these factors [5,6]. It is, therefore, possible that the inhibitory effect of MoAb $NDA_3$ on this B cell response is mediated through blocking of BCGF synthesis or through blocking of BCGF-R expression. The observations that MoAb $NDA_3$ stimulates the growth of cells which have been already activated by SAC suggests that the later possibility is more likely, i.e. that the antibody binds to a receptor site.

MoAb $NDA_3$ stimulates the growth of EBV-transformed LBCL and inhibits their response to BCGF EBV-transformed B cells produce BCGF and display receptors for such autocrine growth factors. The effect of MoAb $NDA_3$ on low—and high—density cultures of EBV-transformed LBCL was tested to determine whether this antibody mimics and/or competes with BCGF for binding to BCGF-R. The rate of growth of two polyclonal B cells lines, LBCL-RC and LBCL-LY, and of two monoclonal LBCL, one producing IgM, LBCL-3D8, and one producing IgG, LBCL-1C, was tested repeatedly in the presence and in the absence of BCGF or of MoAb $NDA_3$ or of MoAb LC.

Cells from these lines grew exponentially when seeded at high density ($5 \times 10^4$/ml) as described by others [7]. However, in the absence of exogenous BCGF, cells seeded at low density (0.5 to $1 \times 10^4$) have a lag period of 72 to 96 hours before starting to grow exponentially. The rate of growth exhibited by low density cultures increases significantly in medium supplemented with BCGF—containing supernatants collected from high density cultures [9]. Low density cultures from all of these LBCL also displayed enhanced proliferation when tested in medium containing MoAb $NDA_3$. As in the case of BCGF, the growth stimulating effect of MoAb $NDA_3$ was evident only when cells were tested at low densities. The growth of LBCL in medium supplemented with MoAb LC was identical to that in medium without MoAb or exogenous BCGF.

Figure 1A:
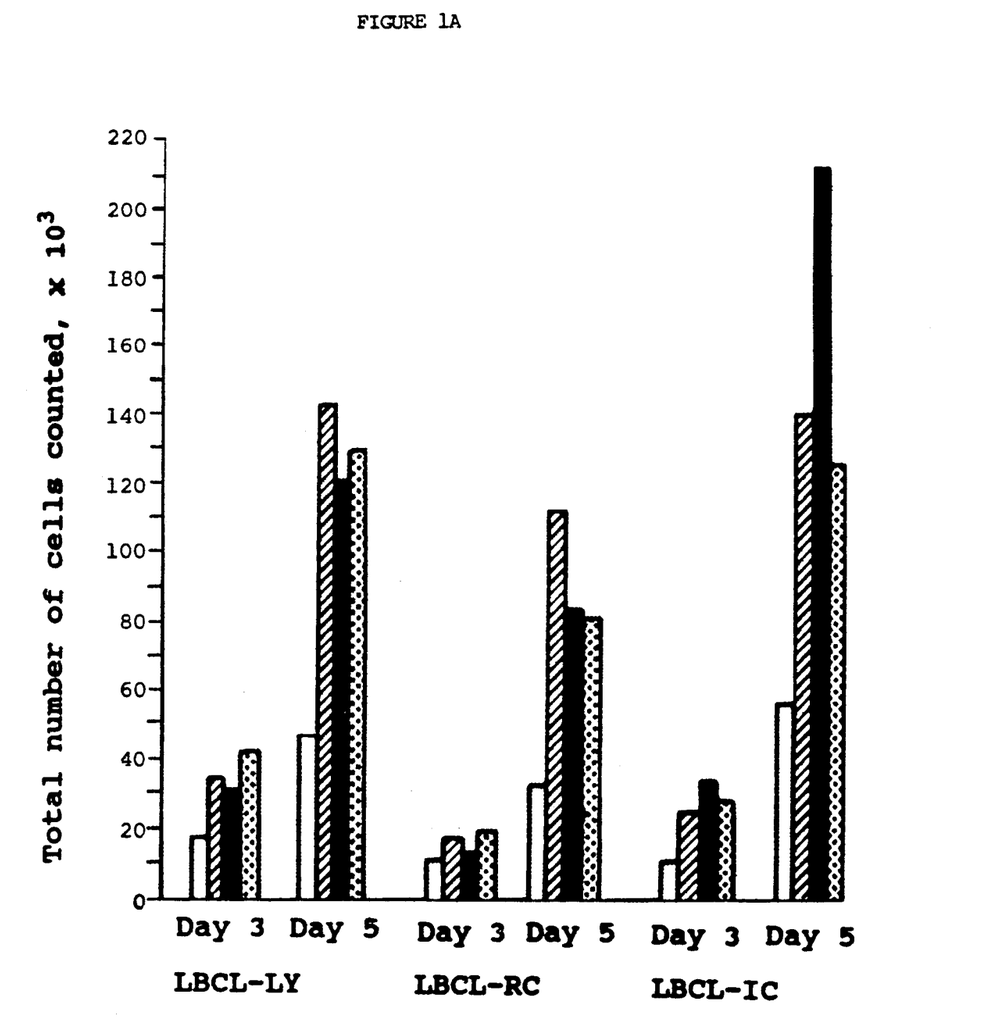
FIG. 1a—Effect of BCGF and MoAb NDA$_3$ on the growth of LBCL.
Figure 1B:
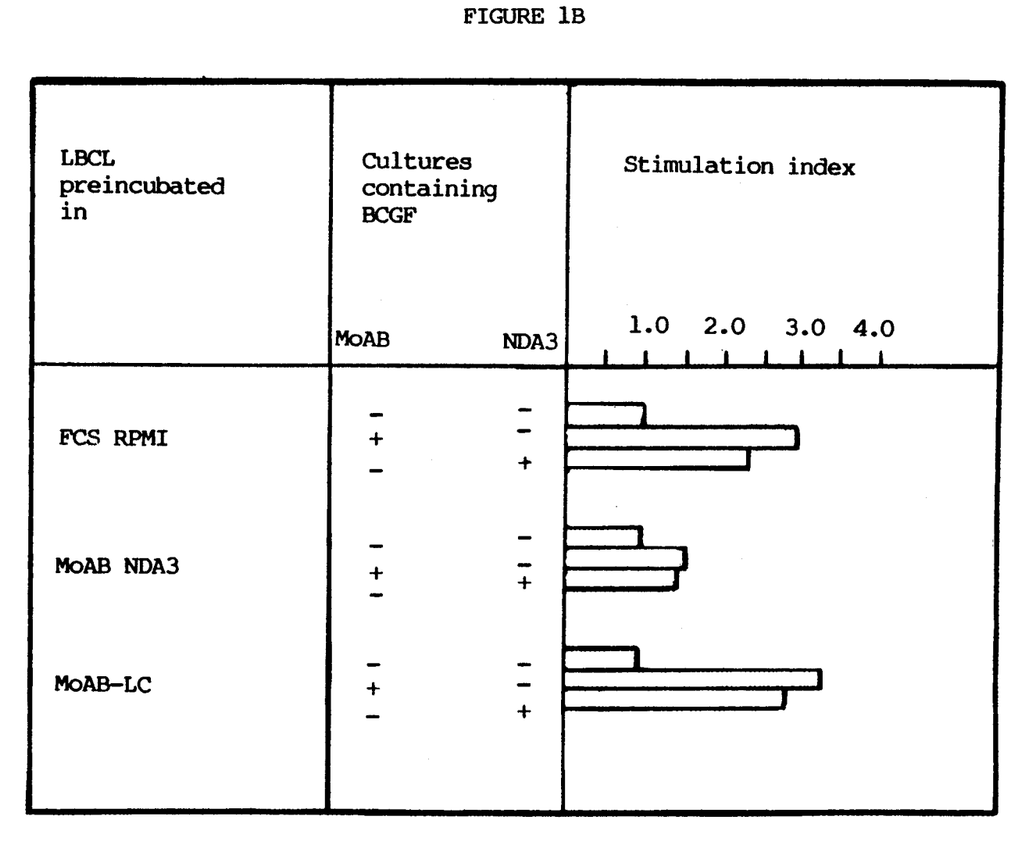
FIG. 1b—Blocking of the growth promoting activity of BCGF by MoAb NDA$_3$.

The growth promoting effect of MoAb $NDA_3$ was of the same order of magnitude as that observed in the presence of autologous BCGF. There was no additive effect, however, between BCGF and MoAb $NDA_3$ when tested together, suggesting that they compete for binding to the same receptor molecule (FIG. 1a.). Supporting this possibility were experiments in which LBCL were first incubated with MoAb $NDA_3$ or with the control MoAb LC, then washed and tested for their responsiveness to BCGF. Pretreatment with MoAb $NDA_3$ but not with MoAb LC inhibited significantly their growth in medium supplemented with BCGF as determined by cell counting (FIG. 1b.). MoAb $NDA_3$ seemed, therefore, to have blocked the receptors for BCGF.

MoAb $NDA_3$ has no direct effect on the rate of immunoglobulin synthesis

The increased rate of proliferation of LBCL grown with MoAb $NDA_3$ was paralleled by an increase rate and amount of Ig synthesis as quantitated by ELISA [16]. For example LBCL-3D8 plated at $5 \times 10^3$ cells/ml in medium without MoAb $NDA_3$ produced 3,000 and 14,250 ng IgM/ml after 3 and 5 days in culture, respectively. In the presence of MoAb $NDA_3$ the corresponding amounts were 3,750 and 20,000 ng IgM/ml.

Figure 2:
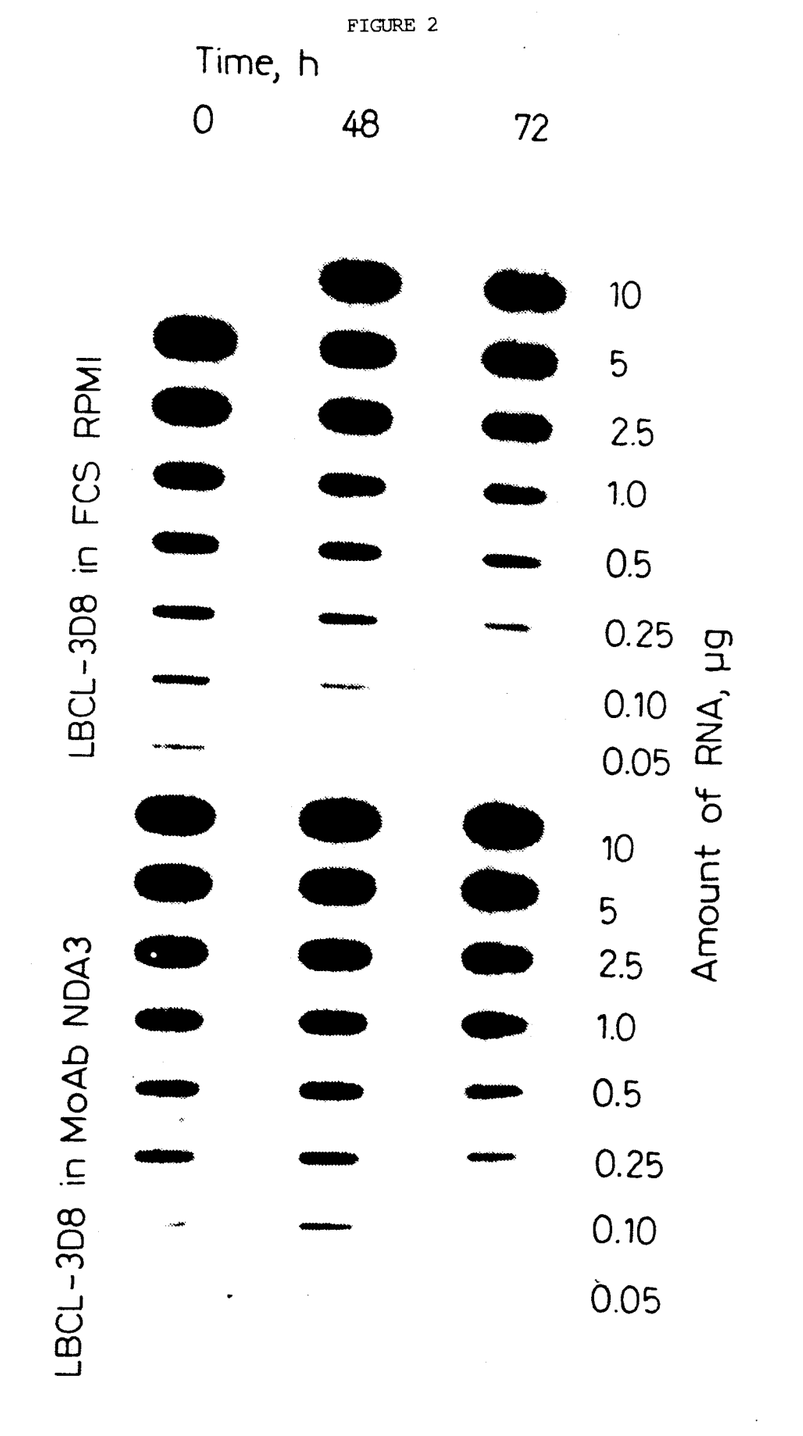
FIG. 2—Density of bands corresponding to equal amounts of RNA from cells grown with or without MoAb NDA$_3$.

To establish whether MoAb $NDA_3$ stimulates the amount of Ig synthesis per cell or merely increases the rate of proliferation, the amount of μ chain gene transcription in the monoclonal IgM producing LBCL-3HB was determined. Hybridization with a probe for the μ region of the heavy chain of human Ig [20] showed no differences in the density of the bands corresponding to equal amounts of RNA [14] from cells grown with or without MoAb NDA$_3$ (FIG. 2) This suggests that the receptor recognized by MoAb NDA$_3$ is related to a factor which promotes growth rather than IgM synthesis. It is unlikely that MoAb NDA$_3$ acts on B cells by cross-linking the Ig receptors, as is the case for anti-IgM induced B cells proliferation, since both IgM and IgG producing monoclonal B-cells lines were equally susceptible to its effect. It is possible that stimulation or inhibition of growth by MoAb NDA$_3$ may be determined by changes in the aggregation state of BCGF-R. This may be part of the process of internalization and degradation of the receptor—ligand complex involved in signal transduction [21].

Structural characterization of cell surface molecules recognized by MoAb NDA$_3$ Immunoprecipitation studies of $^{125}$I-labelled cell membranes [15] from LBCL showed that MoAb NDA$_3$ precipitates under both reducing and non-reducing conditions, a single 36 kd band. After reduction, there was also an additional faint band of approximately 35 kd, suggesting heterogeneity, possibly caused by glcosylation. Preliminary evidence from Western blot studies support this possiblity.

EXAMPLE 6

To characterize the nature of the corresponding epitope, MoAb NDA$_3$ was tested for its effect on the process of B cell activation and proliferation. BCGF used in the following experiments was from the source used for characterization of BCGF-12 kd (Cellular Products, Buffalo, N.Y.).

Since human B cells can be activated by surface Ig cross-linking with anti-$\mu$ antibody or SAC (4) or by stimulation with conditioned media containing BCGF-12 kd [6-10], the blastogenic response of resting, peripheral blood B lymphocytes to these agents in the absence and in the presence of MoAb NDA$_3$ was compared. Blastogenesis was measured in a 3-day assay by determining the amount of tritiated thimidine ($^3$H-TdR) incorporation.

B cells grown for 66 hours in the presence of MoAb NDA$_3$ showed significantly lower responses to stimulation by SAC, BCGF, and BCGF together with anti-$\mu$ than B cells grown without antibody. In the absence of BCGF the response to anti-$\mu$ was not affected by MoAb NDA$_3$.

TABLE 2

Effect of MoAb NDA$_3$ on Human B Lymphocytes

| MoAb added to cultures | Reactivity (mean cpm) in cultures with | | | | |
|---|---|---|---|---|---|
| | Medium only | SAC | Anti-$\mu$ only | Anti-$\mu$ + BCGF | BCGF |
| None | 2685 | 40390 | 7506 | 23394 | 12922 |
| NDA$_3$ | 1074 | 16833 | 7042 | 13604 | 5338 |
| NG-B2 | 1830 | 42250 | 7810 | 24500 | 12400 |

PBL were obtained from fresh peripheral blood by Ficoll-Hypaque gradient centrifugation followed by monocyte depletion through adherence to plastic for 16 hours at 37° C. B cells were purified on a nylon wool column and high density cells were obtained by centrigutation on a discontinuous Percoll gradient (30%, 50%, and 100%) at the interphase between the 50% and 100% layer. The purity of the B cell suspension was greater than or equal to 96% as determined by immunofluoresence analysis of surface immunoglobulin staining. Resting high density B cells (Br) were suspended at $2 \times 10^6$ per ml in RPMl 1640 medium supplemented with glutamine, antibiotics and 10% fetal calf serum (10% FCS). Br were plated at $2 \times 10^5$ cells/well in 96-flat bottom wells. SAC activation was induced by adding to the cultures 0.1 ml of 0.1% SAC. Anti-$\mu$ activation was induced by adding to the cultures goat-anti-$\mu$ F(ab)2 (Cappel Laboratories, Cochranville, Pa.) coupled to Sepharose at a final concentration of 20 $\mu$g/ml. BCGF (10%) was added 24 hours after the initiation of the cultures. MoAb NDA$_3$ and MoAb Ng-B2 were used at a final concentration of 10 pg/ml. Cultures stimulated with SAC received the MoAbs from the start, while cultures stimulated with anti-$\mu$ and/or BCGF received the antibodies after 24 hours. Purified Ig from MoAb was free of mycoplasma as determined by hybridization with $^3$H-DNA probe homologous to Mycoplasma and Acholeplasma ribosomal RNA (Mycoplasma TC Detection Kit, Gen-Probe, San Diego, Calif.). There were no endotoxins in the Ig solution as measured by use of the Limulus Amebocyte Lysate Pyrotell test (Associates of Cape Cod, Inc., Woods Hole, Mass.).

All cultures were labeled with $^3$H-TdR after 48 hours and harvested 18 hours later.

Results are expressed as mean cpm of triplicate reactions. The difference between triplicates were less than 10%.

EXAMPLE 7

Because SAC-activation triggers the production of endogenous BCGF, which amplifies proliferation [4,11], the inhibitable response appears to be that to endogenous or exogenous BCGF. Such inhibition may reflect blocking of a receptor for BCGF by MoAb NDA$_3$, in a manner analogous to blocking of the Interleukin-2 receptor of activated T cells by anti-Tac antibodies [12]. To explore this possibility, B cells activated with SAC or anti-$\mu$ in 48 hour cultures, and EBV-transformed B cells, were preincubated with MoAb NDA$_3$ for 30 minutes in the cold, washed and then tested for their response to BCGF.

Pretreatment with MoAb NDA$_3$ inhibited strongly the response of activated B cells (Ba) to BCGF. The degree of suppression of the response to BCGF was similar when SAC-activated B cells were preincubated in the cold with 10% BCGF or with MoAb NDA$_3$ (Table 3). These findings suggest that the BCGF receptor of activated B cells are effectively blocked by pre-exposing the cells either to the ligand (BCGF) or to MoAb NDA$_3$.

TABLE 3

Effect of MoAb NDA$_3$ on Activated Human B Lymphocytes
Reactivity (mean cpm) in culture with:

| Responding cells | Medium Only | BCGF 10% | BCGF pre-absorbed on cells pre-treated with MoAb: | | MoAb: | |
|---|---|---|---|---|---|---|
| | | | NDA$_3$ | Ng-B$_2$ | NDA$_3$ | Ng-B$_2$ |
| SAC-activated B cells | | | | | | |
| Not pre-treated | 10826 | 65619 | 48141 | 15031 | 32262 | 11200 |
| Pre-treated with: | | | | | | |
| MoAb NDA$_3$ | 5901 | 12014 | 14382 | 13052 | 6420 | 8430 |
| MoAb Ng-B$_2$ | 11420 | 63420 | 51610 | 12180 | 38500 | 10780 |
| 10% BCGF | 12310 | 16464 | 16602 | 10190 | 6829 | 12500 |
| Anti-μ activated B cells | | | | | | |
| Not pre-treated | 26228 | 53590 | 50612 | 25220 | 43395 | 25400 |
| Pre-treated with: | | | | | | |
| MoAb NDA$_3$ | 22720 | 34860 | 30420 | 28510 | 30340 | 26700 |
| MoAb Ng-B$_2$ | 25970 | 57680 | 45862 | 22440 | 46728 | 23680 |
| EBV-transformed B cells | | | | | | |
| Not pre-treated | 1060 | 9910 | 8200 | 1500 | 6218 | 1040 |
| Pre-treated with: | | | | | | |
| MoAb NDA$_3$ | 1210 | 4200 | 3560 | 1320 | 3210 | 2600 |
| MoAb Ng-B$_2$ | 1180 | 10740 | 9500 | 1040 | 7580 | 1410 |

To test the effect of MoAb NDA$_3$ on B cells activated with SAC or with anti-μ, cells were grown with the stimulating agent for 48 hours, then washed, counted and plated at $2 \times 10^5$ viable B-blasts per well. Responding cells were pre-treated with MoAb (at 10 μg/ml) or with 10% BCGF by incubation at 4° C. for 30 minutes, followed by two washings. BCGF was absorbed on SAC activated B-cells by incubating 10% BCGF with $10^7$ activated B cells per ml for 30 minutes in the cold. Cells were pelleted and the supernatant was collected and used as absorbed BCGF. Prior to use for absorbtion, SAC-activated B cells were pre-treated with MoAb NDA$_3$ or with MoAb Ng-B2 for 20 minutes as described above. EBV-transformed B cells were grown in continuous cultures. Prior to use, cells were harvested from the culture, washed, counted, adjusted to $25 \times 10^3$/ml and plated in a total volume of 0.2 ml. All cultures were labelled with tritiated thymidine after 64 hours and harvested 8 hours later.

EXAMPLE 8

Further proof that MoAb NDA$_3$ blocks the receptor for BCGF of activated B cells was obtained by testing the possibility that blocking of the BCGF receptor may abolish the capacity of activated, receptor-bearing B cells to absorb BCGF. For this, SAC-activated B cells were preincubated for 30 minutes in the cold with MoAb NDA$_3$ or with a control antibody specific for human beta-2 microglobulin, washed and then used for absorbtion of BCGF (10%). BCGF absorbed on SAC-activated B cells, whose BCGF receptors were presumably blocked by the putative anti-receptor MoAb NDA$_3$, showed very little reduction of growth promoting activity when tested on cells activated by SAC, anti-μ or EBV-infection. In contrast, BCGF absorbed on SAC-activated B cells that have been treated under the same conditions with an irrelevant MoAb showed little residual activity, indicating that its growth promoting activity has been indeed removed by absorbtion with activated cells see (Table 3).

EXAMPLE 9

Although pre-exposure of activated B cells to MoAb NDA$^3$ inhibits their capacity to respond to BCGF, this antibody stimulates proliferation when added to cultures of SAC, anti-μ or EBV-activated B cells (Table 3). This effect suggests that by binding to the BCGF-receptor, the antibody can mimic the ligand (BCGF). Neither BCGF or MoAb NDA$_3$ triggered proliferation when added to cultures of activated cells whose receptors for BCGF have been blocked by pretreatment with MoAb NDA$_3$.

The possibility that the antigen recognized by MoAb NDA$_3$ is structurally identical with, or at least sterically very close to the receptor for human BCGF-12 kd was tested by blocking the receptor with either BCGF or with MoAb NDA$_3$ and then examining the ability of B cells to bind radiolabelled antibody, MoAb NDA$_3$. See FIG. 3.

MoAb NDA$_3$ was purified from culture supernatants by gel filtration through Sephacryl S-300 superfine (Pharmacia). The flow through fraction was tested by ELISA using anti-mouseμ to determine the concentration of IgM. The fraction of NDA$_3$ which may be inhibited from binding by an excess of "cold" NDA$_3$ was determined by adding to a standard number of lymphoblasts ($10^6$) a standard quantity of labelled antibody (0.06 μg, containing $5 \times 10^5$ CPM) alone or in the presence of 1 or 10 μg of cold antibody. The "inhibitable" or "specific" fraction of the labelled reagent was 50% of the total CPM bound.

Inhibition by cold antibody, by BCGF and by an unrelated monoclonal antibody (NDA$_9$-anti-transferrin receptor) is expressed with reference to "inhibitable" or "specific" CPM. For these experiments, MoAb NDA$_3$ was purified as above and BCGF was separated by FPLC on a sepharose 12 column (Pharmacia) from a stock provided by Dr. Mehta [10]. Purity of the active fraction, $M_r=12$ kd, was monitored by SDS-PAGE (12.5% gels) and its concentration by spectroflorometry (OD=280) [10]. MoAb NDA$_9$, an IgG1 antibody, was purified from supernatants by affinity-chromatography on BioRad's Affinity Gel Protein A.

Labelling was performed using Iodo-gen ® (Pierce Chemical Co., Rockford Ill.); 25 μg of Iodo-gen ® were used to label 50 μg of protein in 300 μl with 500 μCi of $^{125}$I (Amersham, Ill.). Binding of labelled NDA$_3$ was conducted using $10^6$ cells and 0.06 μg of labelled NDA$_3$ in the presence (or absence) of the inhibitor indicated in FIG. 3.

Volume was kept constant (1 ml) with RPMI 1640 containing lyzozyme (0.1%). All experiments were conducted in triplicate and results are expressed as the respective means. All binding and inhibition experiments were conducted at 4° C. and each incubation phase was 2 h.

The results shown in FIG. 3 are consistent with this hypothesis, since the binding of the labelled MoAb $NDA_3$ was significantly reduced in the presence of BCGF-12 kd. The controls, cold $NDA_3$ and the anti-transferrin-receptor antibody $NDA_9$, had inhibitory and neutral effects, respectively, on the binding of $NDA_3$. Similarly, IL-2 was not inhibitory (data not shown). From the specific activity of the labelled antibody and the amount specifically bound at the concentration chosen (0.06 µg), the number of sites was calculated to be 14,000 +/−2000. Scatchard analyses (not shown) yielded a remarkably close estimate, 12,300 +/−1,700 sites per cell, for this particular cell line. These estimates are not very far from those obtained by Mehta et al. [10] for the high-affinity receptors $(4-8 \times 10^3)$ using the natural ligand BCGF-12 kd. Low-affinity receptors were found to be more numerous, however. The estimates are based on an assumed antibody valence of 1, which may not be numerically accurate given the pentameric nature of IgM: the proximity of the receptor sites on the cell surface will determine whether they lie within bridging distance by IgM. Additionally, the number of BCGF-12 kd receptor sites varies considerably within the same B cell line in a manner apparently unrelated to the cell cycle (data not shown). These variations may depend on the autocrine production of growth factors.

EXAMPLE 10

The comparatively large number of IgM antibody molecules bound per cell is within the sensitivity range of ELISA techniques. Thus, the binding of MoAb $NDA_3$ on insolubilized lymphoblastoid cell membranes and its blocking by BCGF was tested as described in Table 4 below. In these experiments, a constant amount of BCGF (unpurified, 10% dilution) was used to block the binding of MoAb $NDA_3$ in different concentrations. The controls included an unrelated ligand, IL-2, and an unrelated antibody, L243 which reacts with human Ia in the target membranes [13]. As in the previous experiment, BCGF reduced the binding of $NDA_3$, by more than half at the lowest antibody concentration used. IL-2 was neutral and neither ligand blocked the binding of L243.

Therefore, the binding of MoAb $NDA_3$ to its target molecules can be easily and specifically blocked by BCGF in both native solutions and purified forms. The $NDA_3$-binding molecules is thus, the putative BCGF receptor.

TABLE 4

Inhibition of MoAb $NDA_3$ Binding to Soluble B Cell Extracts by BCGF in ELISA

| MoAb tested concentration µg/ml | Cell membranes incubated with: | | |
|---|---|---|---|
| | PBS | BCGF | IL-2 |
| | OD (mean of triplicate reactions) | | |
| $NDA_3$ 10 | 538 | 396 | 532 |
| $NDA_3$ 5 | 415 | 257 | 400 |
| $NDA_3$ 2.5 | 323 | 140 | 235 |
| L243 1 | 912 | 925 | 903 |
| L243 .5 | 844 | 895 | 799 |

TABLE 4-continued

Inhibition of MoAb $NDA_3$ Binding to Soluble B Cell Extracts by BCGF in ELISA

| MoAb tested concentration µg/ml | Cell membranes incubated with: | | |
|---|---|---|---|
| | PBS | BCGF | IL-2 |
| L243 .25 | 759 | 767 | 701 |

Cell membrane extracts were prepared as described above and dialysed against PBS for 1 hour at 4° C. Microwell plates (Immulon, Dynatech Lab., Alexandria, Va.) were coated with 20 µg/ml of the cell membrane extract in carbonate-bicarbonate buffer (pH 9.0) at room temperature for 18 hours.

Nonspecific binding sites were blocked for 2 hours at 37° C. with 0.5% casein in PBS and washed twice with 0.1% Tween 20 (PBS-Tween). Two hundred microliters of 10% BCGF or 20% IL-2 (Lymphocult, Biotest, Germany) in PBS with 0.5% casein were added to the wells. Following 2 hours of incubation at 37° C., the plates were washed with PBS/Tween three times. Various concentrations of MoAb $NDA_3$ or MoAb $L_{243}$ in PBS with Casein were added to the wells. Plates were incubated for 2 hours at 37° C., and then washed three times in PBS/Tween. Biotinylated goat anti-mouse IgM (Vector Research, Burlingame, Calif.) at 1 µg/ml in PBS/Tween containing 0.5% casein was added. After 2 hours at 37° C. plates were washed and streptavidin-biotinylated peroxidase complex (Vector Laboratories) diluted 1:1000 in PBS/Tween with casein was added. Incubation was continued for an additional hour at 37° C., then plates were washed twice and then incubated at room temperature in the dark with a 12% solution of o-phenylenediamine in McIlvain's buffer (pH 6.0) containing 0.05% $H_2O_2$. The absorbance of the wells was determined at 492 nm in a Dynatech-Autoreader MR 580.

EXAMPLE 11

The $NDA_3$-binding molecule was characterized by conventional immunoprecipitation. Cell surface proteins were labelled with $^{125}$Iodine (Amersham, Ill.) using the lactoperoxidose (Sigma, Mo.) method (14). After labelling, cells were washed in PBS, and then lysed by treatment with 1% Nonidet P-40 (Sigma) in 10 mM Tris-HCL buffer (pH 8.2) with 150 mM NaCl, 0.1% lysozyme (Sigma), and 1 mM phenylmethyl-sulphonyl fluoride (PMSF), (Sigma) for 30 minutes on ice. The lysate was centrifuged for 1 hour at 50,000 g. Aliquots of radio-labelled lysate were precleared by incubation at 4° C. for 1 hour with rabbit anti-mouse IgM coupled to CNBr-activated Sepharose 4B, followed by 10 minutes of centrifugation in the cold at 12,000 g. The preclearing was repeated two more times. The precleared cell lysate supernatant was incubated for 2 hours at 4° C. with purified MoAb $NDA_3$ attached to CNBr-activated Sepharose 4B (Pharmacia, Uppsala, Sweden). The precipitate was centrifuged at 10,000 rpm for 10 minutes at 4° C. The pellet was washed three times in 0.5 M NaCl lysis buffer (pH 8.2) and then dissolved in SDS-PAGE sample buffer (Tris-HCL, pH 6.8) with or without 2% 2-mercaptoethanol. Immunoprecipitates were then processed for SDS-polyacrylamide gel electrophoresis using vertical slab gels and the Laemmli (1970) buffer system. The concentration of running gel was 12.5% and that of the stacking gel was 3%. Electrophoresis was performed at 30 mA per gel. The gel was developed, dried and then autoradiographed with Kodak XAR-5 film. The internal molecular weight markers were: Phosphorylase B (92.5 kd), bovine serum albumin (66.2 kd), ovalbumin (45 kd), carbonic anhydrase (31 kd), soybean trypsin inhibitor (21.5 kd) and lysozyme (14 kd) (Bio-Rad, Richmond, Calif.). Lane a shows the molecule precipitated by MoAb NDA$_3$ under reduced conditions, lane b shows that rabbit anti-mouse IgM reacts with actine (45 kd) when tested on precleared supernatants from cell lysates.

Figure 4:
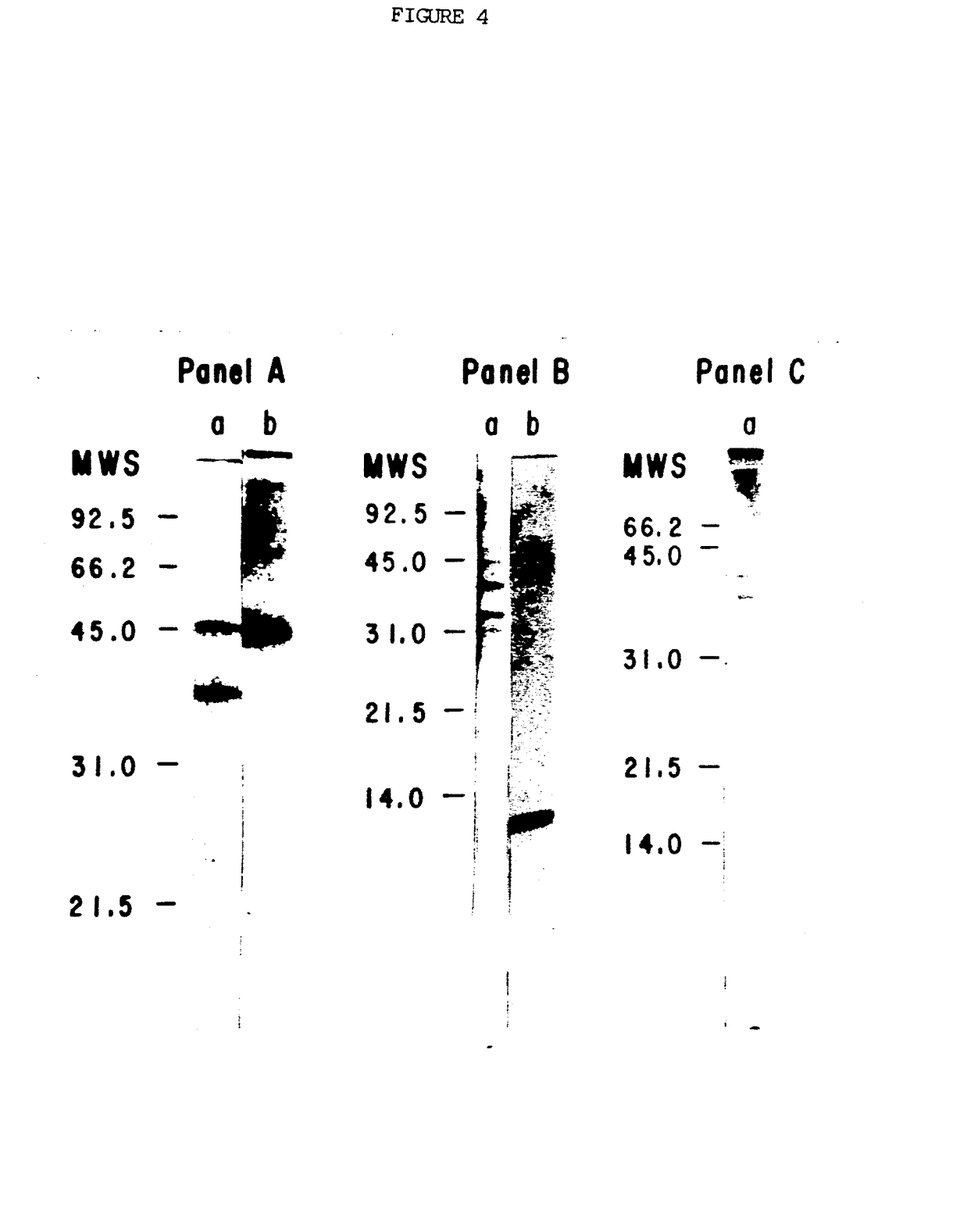

The SDS-PAGE electrophoresis using immunoprecipitated, $^{125}$I-labelled extracts from EBV-transformed lymphoblastoid cell lines yielded 36 kd band (see FIG. 4, Panel A).

EXAMPLE 12

An identical protein band was found in the Western blot analysis using either directly iodinated MoAb NDA$_3$ or enzyme-conjugated second antibody, confirming the existence of the 36 kd-band. An additional band of approximately 32 kd was also found consistently, which may represent, among several possibilities, a degradation product of the 36 kd band or incompletely glycosylated form of the same protein (FIG. 4, Panel B and Panel C).

In FIG. 3, Panel B, $10^8$ cells were washed three times in PBS, then resuspended in 5 ml of 20 mM Tris-HCl buffer (pH 7.4) containing 1 mM PMSF and homogenized. The extract was centrifuged at 3000 g for 10 minutes at 4° C., and the supernatant was collected and ultracentrifuged at 100,000 g for 1 hour in the cold. The pellet was dissolved in 0.5% Nonidet P-40 in 20 mM Tris-HCl buffer (pH 7.4) during 30 minutes on ice and ultracentrifuged at 100,000 g for 1 hour in the cold. The supernatant containing solubilized membrane fractions was electrophoresed in sample buffer containing 2-mercaptoethanol at constant voltage of 120 V on a 12.5% SDS gel. The proteins were transferred to nitrocellulose paper in 190 mM glycine-Tris (25 mM) buffer containing methanol (12.5% v/v). Electroblotting was performed at 4° C. at constant current of 170 mA, for 16 hours. Molecular weight markers were visualized by staining the filters directly with Poinceau S (Sigma Chem. Corp., St. Louis, Mo.). The other strips containing membrane proteins were blocked with 5% BSA for 1 hour at 37° C., covered with MoAb NDA$_3$ (line a) or with MoAb anti-beta-2 microglobulin (line b). After two hours of incubation at 37° C., under continuous shaking, the strips were washed and stained with peroxidase conjugated rabbit-anti-mouse-IgM antibody (Jackson Lab, Avondale, Pa.) diluted 1 to 5000 in 1% BSA-PBS. Following 1 hour of incubation at room temperature, 2,2-azino-di(3-ethylbenzthiazoline sulfonic acid) (ABTS) (Zymed Lab, San Francisco, Calif.), was added as a substrate.

In Panel C, cell membrane extracts were prepared and transferred to nitrocellulose filters as above. Filters were covered with $^{125}$I-labelled MoAb NDA$_3$, then incubated for 1 hour at room temperature, washed five times with 1% BSA in PBS, dried, and autoradiographed using Kodak XAR-5 film (line c).

Results of the blocking studies indicate that this 36 kd molecule identified by MoAb NDA$_3$ is the human B cell receptor for BCGF-12 kd, a factor which stimulates B cell proliferation. The NDA$_3$ antigen is expressed by activated, normal human B cells as well as by EBV-transformed LBCL and may serve as a receptor for both endogenous and exogenous (re: T-cell produced) BCGF.

REFERENCES

1. Muraguchi, A., Bulter, J. R., Kehrl, J. H. and Fauci, A. S., Differential Sensitivity of Human B Cell Subsets to Activation Signals Delivered by Anti-μ Antibody and Proliferative Signals Delivered by a Monoclonal B Cell Growth Factor; J. Exp. Med. 15/: 530–546 (1983).
2. Yoshizaki, K., Nakagawa, T., Kaleda, T., Muraguki, A., Yamamura, Y., Kishimoto, T., Induction of Proliferation and Ig Production in Human B Leukemic Ceiis by Anti-immunoglobulin and T Cell Factors; J. Immunol. 128: 1296–1301 (1982).
3. Viteta, E. S., 0'Hara, J., Myers, C. D., Layton, J. E., Krammer, P. H., Paul, W. E., Serological, Bio-Chemical and Functional Identity or B-cell Stimulatory Factor 1 and B cell Differentiation Factor for IgGl, J. Exp. Med. 162: 1726–1731 (1985).
4. Cambier, J. C., Seeing the Way to B-cell Growth, Nature 319: 620 (1986).
5. Jurgensen, C. H., Ambrus, J. L., and Fauci, A. S., Production of B Cell Growth Factor by Normal Human B Cells, J. Immunol. 136: 4542–4547 (1986).
6. Muraguchi, A., Nishimoto, H., Kawamura, N., Hori, A. and Kishimoto T., B Cell Derived BCGF Functions as Autocrine Growth Factor(s) in Normal and Transformed B Lymphocytes, J. Immunol. 137: 179–186 (1986).
7. Blazar, B. A., Sutton, L. M. and Strome, M., Self-stimulating Growth Factor Production by B Cell Lines Derived from Burkitt's Lymphomas and Other Lines Transformed in vitro by Epstein-Barr Virus, Cancer Res. 43:4562–4566 (1983).
8. Gordon, J., Ley, S. C., Melamed, M. D., Aman, P., Hughes, N. C., Soluble Factor Requirements for the Autostimulatory Growth of B Lymphoblasts Immortalized by Epstein-Barr Virus, J. Exp. Med. 159: 1554–1559 (1984).
9. Gordon, J., Ley, S. C., Melamed, M. D., English, L. S., Hughes, N. C., Jones, Immortalized B Lymphocytes Produce B-cell Growth Factor, Nature 310: 145–147 (1984).
10. Muraguchi, A., Kishimoto, T., Miki, Y., Kuritani, T., Kaieda, T., Yoshizaki, K., Yamamura, Y., T-cell Replacing Factor (TRF)-Induced IgG Secretion in a Human B Blastoid Cell Line and Demonstration of Acceptors for TRF, J. Immunol. 127: 412–416 (1981).
11. Haars, R., Rohowsky-Kochan, C., Reed, E., King, D. W., Suciu-Foca, N., Modulation of T-cell Antigen Receptor on Lymphocyte Membrane, Immunogentics 20: 397–405 (1984).
12. Goding, J. W., Conjugation of Antibodies with Fluorochromes: Modification of the Standard Methods, J. Immunol. Meth. 13: 215–226 (1976).
13. Salacinski, P. R. P., McLean, C., Sykes, J. E., Clement-Jones, V. V., Lowry, P. J., Iodination of Proteins, Glycoproteins and Peptides Using a Solid-phase Oxidizing Agent, 1, 3, 4, 6-Tetrachloro-3d, 6d-diphenyl glycoluril (iodogen), Anal. Biochem. 117: 136–146 (1961).
14. Chirgivin, J. M., Przybyla, A. E., MacDonald, J., Rutter, W. J., Isolation of Biologically Active Neonucleic Acid from Sources Enriched in ribonuclease, Biochemistry 18: 5294–5299 (1979).

15. Laemmli, U. K., Cleavage of Structural Proteins During the Assembly of the Head of Bacteriophage T4, Nature 227: 680–685 (1970).
16. Suciu-Foca, N., MacKenzie, W., Ng, A., Cai, J. and King, D. W., A Late Differentiation Antigen Associated with the Helper Inducer Function of Human T Cells, Nature 318: 465–467 (1985).
17. Welte, K., Andreeff, M., Platzer, E., Holloway, K., Rubin, B. Y., Moore, M. A., Mertelsmann, Interleukin 2 Regulates the Expression of Tac Antigen on Peripheral Blood T Lymphocytes, J. Exp. Med. 160: 1390–1402 (1984).
18. Roth, P., Halper, J. P., Weinstein, B., Pernis, B., A Phorbal Oster Tumor Promoter Induces Changes in the Expression of Immunoglobulins and DR Antigens in Human Lymphoblastoid Cells, J. Immunol 129: 539–544 (1982).
19. Weinstein, I. B., Arcoleo, J., Lambert, M., Hsiao, W., Gattoni-Celli, S., Jeffrey, A. M., Kirschmeier, P., Molecular Mechanisms of Multistage Chemical Carcinogensis, in Progress in Cancer Research and Therapy, Vol. 32, Molecular Biology of Tumor Cells, Wahren, B., Holm, G., Hammarstrom, S., Perlman, P., Editors, (Raven Press, New York 1985).
20. Ravetch, J. V., Siebenlist, U., Korsmeyer. S., Waldmann, T., Leder, P., Structure of the Human Immunoglobulin u Locus: Characterization of Embryonic and Rearranged J and D Genes, Cell 27: 583–591 (1981) Part 2.
21. Schreiber, P., Lax, I., Yarden, Y., Eshhar, Z., Schessinger, J., Monoclonal Antibodies Against Receptor for Epidermal Growth Factor Induce Early and Delayed Effect of Epidermal Growth Factor, Proc. Natl. Acad. Sci. USA 78: 7535–7539 (1981).
22. Clark, E. A., Shu, G., Ledbetter, J. Role of the Bp35 Cell Surface Polypeptide in Human B Cell Activation, Proc. Natl. Acad. Sci. USA 82: 1766–1770 (1985).
23. Jung, L. K. L., Fu, S. M., Selective Inhibition of Growth Factor Dependent Human B Cell Proliferation by Monoclonal Antibody AB1 to an Antigen Expressed by Activated B Cells, J. Exp. Med. 160: 1919–1924 (1985).
24. Kikutani, H. Kimura, R., Nakamura, H., Sato, R., Muraguki, A., Kawamura, N., Hardy, R. R., Kishimoto, T., Expression and Function of an Early Activation Marker Restricted to Human B Cells, J. Immunol. 136: 4019–4026 (1986).
25. Mishra, G. C., Berton, M. T., Oliver, K. G., Kramer, P. H., Uhr, T. W., Viteta, E. S., A Mouse LFA-1 Antibody Mimics the Biological Effects of B Cell Stimulatory Factor-1 (BSF-1), J. Immunol. 137: 1590–1598 (1986).
26. Waldman, T. A., The Structure, Function and Expression of IL-2 Receptors on Normal and Malignant Lymphocytes, Science, 232: 727–732 (1986).
27. Tedder, T. F., Boyd, A. W., Freedman, A. S., Nadler, L. M., Schlossman, S. I., The B Cell Surface Molecule B1 is Functionally Linked with B Cell Activation and Differentiation, J. Immunol. 135: 973–976 (1985).

What is claimed is:

1. A purified differentiation antigen (NDA$_3$) associated with the growth and proliferation of activated B lymphocytes and having a molecular weight of about 36,000 daltons which comprises at least a portion of B cell growth factor receptor specific for BCGF-12 kd and which is present on activated B cells and helper T cells and is immunologically reactive with the monoclonal antibody designated MoAb NDA$_3$ produced by hybridoma ATCC Accession No. HB 9334.

2. A purified differentiation antigen of claim 1, wherein the activated B lymphocytes are human B lymphocytes.

3. An antibody capable of specifically forming a complex with the purified differentiation antigen of claim 1.

4. An antibody of claim 3 which comprises a monoclonal antibody.

5. A hybridoma deposited under ATCC Accession No. HB 9334 which produces the monoclonal antibody of claim 4.

6. A method of detecting activated B cells or helper T cells which comprises:
   a. isolating peripheral blood mononuclear cells;
   b. treating the cells with the monoclonal antibody of claim 4, and
   c. determining the amount of monoclonal antibody bound to the cells.

7. A method for detecting activated B cells or helper T cells, each of which has a B cell growth factor receptor, which comprises contacting a sample which contains activated B cells or helper T cells with the antibody of claim 3 so as to form a cellular complex between the antibody and the B cell growth factor receptor and detecting such cellular complex.

8. A method of detecting the activated B cells or helper T cells according to the method of claim 7, which further comprises determining the number of activated B cells or helper T cells.

9. A method of claim 7, wherein the activated B lymphocytes are human B lymphocytes.

10. A method for diagnosing an immune system abnormality in a subject which comprises determining the percentage of activated B cells or helper T cells in a sample from the subject, contacting the sample with the antibody of claim 3 so as to form a complex between the antibody and B cell growth factor receptor, determining the percentage of activated B cells or helper T cells in the sample which have the B cell growth factor receptor and comparing the percentage so determined with the percentage of cells which have the B cell growth factor receptor in a sample from a normal subject who does not have the immune system abnormality, a difference in the percentage of cells so determined being indicative of the immune system abnormality.

11. A method of claim 10, wherein the subject is a human.

* * * * *